US00PP12683P2

(12) United States Plant Patent
Olesen et al.

(10) Patent No.: US PP12,683 P2
(45) Date of Patent: Jun. 11, 2002

(54) CLIMBING ROSE PLANT NAMED 'POULBOTA'

(76) Inventors: L. Pernille Olesen; Mogens N. Olesen, both of Hillerrodvejen 49, Fredensborg, DK-3480 (DK)

( * ) Notice: Subject to any disclaimer, the term of this patent is extended or adjusted under 35 U.S.C. 154(b) by 0 days.

(21) Appl. No.: 09/276,890

(22) Filed: Mar. 25, 1999

(51) Int. Cl.[7] ..... A01H 5/00

(52) U.S. Cl. ..... Plt./114

(58) Field of Search ..... Plt./114, 109, 110, Plt./112

*Primary Examiner*—Bruce R. Campell
*Assistant Examiner*—June Hwu

(57) ABSTRACT

A new garden rose plant which has abundant, blush flowers with colorful stamens, vigorous growth and attractive foliage. This new and distinct variety has shown to be uniform and stable in the resulting generations from asexual propagation.

2 Drawing Sheets

SUMMARY OF THE INVENTION

The present invention constitutes a new and distinct variety of garden rose plant which originated from a controlled crossing between 'Morning Jewel' (non-patented) and an unnamed seedling (non-patented). The two parents were crossed and the resulting seeds were planted in a controlled environment. The new variety is named 'POULbota'.

The new rose may be distinguished from its seed parent, 'Morning Jewel', by the following combination of characteristics:

1. The seed parent has pink flowers; whereas 'POULbota' has blush flowers;
2. The seed parent blooms less frequently than 'POULbota'.

The new variety may be distinguished from its pollen parent, an unnamed seedling created by the same inventors, by the following combination of characteristics:

1. The pollen parent has dark-red flowers, whereas, 'POULbota' has blush flowers.
2. The pollen parent's flowers are very double; whereas, 'POULbota' has semi-double flowers.

The objective of the hybridization of this rose variety for garden use was to create a new and distinct variety with unique qualities, such as:

1. Uniform and abundant flowers;
2. Vigorous growth;
3. Disease resistance;
4. Climbing characteristics.

This combination of qualities is not present in previously available commercial cultivars of this type and distinguishes 'POULbota' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULbota' was selected by the inventors in the spring of 1990 has a single plant from the progeny of aforementioned by hybridization.

Asexual reproduction of 'POULbota' by traditional budding was first done by L. Pernille and Mogens N. Olesen in August, 1991. This initial and other subsequent propagtions conducted in controlled environments have demonstrated that the characteristics of 'POULbota' are true to type and are transmitted from one generation to the next.

BRIEF DESCRIPTION OF THE DRAWING

The accompanying color illustration shows, as true as is reasonably possible to obtain in color photographs of this type, the typical characteristics of the buds, flowers, leaves, and stems, of 'POULbota'. The variety illustrated in SHEET 1 indicates the variety known as 'POULbota' prior to change in designation to 'POULbota' as mandated by the European Union Plant Breeder's Right Office. Specifically illustrated in SHEET 1:

1. Stem of showing branching and the attachment of leaves, buds, and peduncles;

2. Flower bud, partially opened bud, and open bloom;

3. Flower petals, detached;

Specifically illustrated in SHEET 2:

4. Sepals, receptacle, and pedicel;

5. Flowering stem as well as a bare stem exhibiting thorns;

6. Leaves.

DETAILED DESCRIPTION OF THE VARIETY

The following is a description of 'POULbota', as observed in its outdoor growth in a field nursery in Jackson County, Oreg. Observations were conducted during September, 1998, on an eighteen month old plant. Color references are made using The Royal Horticultural Society (London, England) Colour Chart, 1995, except where common terms of color are used. For a comparison, several physical characteristics of the rose variety 'POULbota', a climbing rose variety, from the same inventors, described and illustrated in U.S. Plant Pat. No. 10,639 and issued on Oct. 13, 1998 are compared to 'POULbota' in Chart 1.

CHART I

| | 'POULbota' | 'POULclimb' |
|---|---|---|
| Flowering habit. | Almost continuous. | Almost continuous. |
| Petal count. | Semi-double; 12–14 petals. | Double; 25–30 petals. |
| General bloom. color, when fully open. | Blush. | Striped, old rose pink and creamy white. |

Parents:
*Seed parent.*—'Morning Jewel'.
*Pollen parent.*—Unnamed seedling.
Classification:
*Botanical.*—*Rosa hybrida.*
*Commercial.*—Climber.

FLOWER AND FLOWER BUD

Flower arrangement: Panicle.
Blooming habit: Almost continuous.
Flower bud:
*Size.*—Upon opening, 25 mm in length from base of receptacle to end of bud.
*Bud form.*—Pointed ovoid.
*Bud color.*—As sepals unfold, Orange Group 29C at ¼ opening.
*Sepals.*—Upper side, Green Group 143D. Lower side, Green Group 143D. Small foliaceous appendages on three of the five sepals. Surfaces of sepals slightly pubescent. Stipitate glands are present on margins.
*Receptacle.*—Surface: Smooth. Shape: Urn-shaped. Size: Medium. 7 mm (h)×7 mm (w). Color: Green Group 143C.
*Peduncle.*—Surface: Covered with stipitate glands. Length: 40–50 mm average length. Color: Green Group 143C with intonations on some peduncles of Greyed-Red Group 181B. Strength: Upright.
*Borne.*—4–6 buds per flowering stem. Flowers on new and old wood.
Flower bloom:
*Fragrance.*—Moderate spicy scent for bloom, but the stipitate hairs on the pedicel when touched give off a strong scent of eucalyptus and cloves.
*Duration.*—Flowers last from 3 to 4 days on the plant. Not tested as a cut flower. Petals fall cleanly away from plant. Period of bloom is long.
*Size.*—Medium. Average flower diameter is 70–80 mm when open.
*Form.*—Semi-Double flowers carried in clusters.
*Shape of flower when viewed from the side.*—Upon opening, upper part: Flat. Upon opening, lower part: Convex. Open flower, upper part: Flat. Open flower, lower part: Concave.
*Petalage.*—Semi-double. Average range: 12–14 petals under normal conditions.
Color:
*Upon opening, petals.*—Outermost petals: Upper Surface: Orange Group 27A. Reverse Side: Red Group 36C. Outermost petals exhibit some coloration of Green Group 143C. Innermost petals: Upper Surface: Orange Group 27A. Reverse Side: Red Group 36C.
*Upon opening, basal petal spots.*—Outermost petals: Outer Side: Yellow Group 1B. Inner Side: Yellow Group 4A. Innermost petals: Outer Side: Yellow Group 1B. Inner Side: Yellow Group 5A.
*After opening, petals.*—Outermost petals: Upper Surface: Red Group 36D to Orange-White Group 158C. Reverse Side: Orange Group 27D. Innermost petals: Upper Surface: Red Group 36D. Reverse Side: Red Group 36D.
*After, basal petal spots.*—Petals: Outer Side: Green-Yellow Group 1D. Inner Side: Green-Yellow Group 1D.
General tonality: On open flower Red Group 36D. No change in the general tonality at the end of the 2nd day. Afterwards, general tonality is Orange-White Group 159D.
Petals:
*Petal reflex.*—Petals reflex slightly.
*Petal edge.*—Slightly ruffled with point in center of the margin.
*Shape.*—Round to deltoid shaped. The petal's apex shape is broadly round. Petal's base shape is pointed.
*Petaloids.*—1–2 petaloids. Petaloids are small relative to petals. Petaloids are thin, and colored Yellow Group 4A on the outer side, Yellow Group 1A on the inner side.
*Thickness.*—Above average thickness.
*Arrangement.*—Open, not imbricated.
*Texture.*—Upper surface: Smooth. Lower surface: smooth.
Reproductive organs:
*Pollen.*—Color: Yellow Group 13B. Quantity: Average abundance.
*Anthers.*—Size: On open flower 6 to 10 mm. Color: Immature; Yellow Group 13B, mature; Greyed-Orange Group 163C. Quantity: 30 to 35. Pistils: 10 to 15.
*Filaments.*—Color: Red Group 53B.
*Stigmas.*—Situated at or slightly inferior in location to anthers on open flowers. Color: Greyed-Yellow Group 162C. Length: 7–11 mm.
*Styles.*—Color: Red Group 53C. Length: 10 mm.
*Stamens.*—Color: Greyed-Yellow Group 162C. Length: 4–6 mm.
*Hips.*—None observed.

PLANT

Plant growth: Vigorous, climbing rose. As a budded field grown plant on *Rosa multiflora* understock, the average height of the plant is 300 cm.
Stems:
*Color.*—Young wood: Green Group 146C. Older wood: Green Group 146C.
*Thorns.*—Incidence: Moderate. Size: Average length: 5–6 mm. Color, Immature: Greyed-Purple Group 183C. Mature: Greyed-Purple Group 172C. Shape: Concave with a downward curve.
*Surface.*—Young wood: Smooth. Older wood: Smooth.
Plant foliage: Normal number of leaflets on leaves in middle of the stem: 5 leaflets.
*Leaf size.*—Large. 140–150 mm (l)×90–100 mm (w).
*Quantity.*—Average.
*Color.*—Upper Leaf Surface: Green Group 137A. Lower Leaf Surface: Yellow-Green Group 146C. Juvenile foliage: Yellow-Green Group 146A. Anthocyanin: Moderate. Location: All new growth. Upper and lower surfaces of leaflets, leaflets margins, petioles, rachis, stipules, stems, and thorns. Color:

Bronze portions are Greyed-Orange Group 175C. Red portions are Greyed-Purple Group 183C.

Plant leaves and leaflets:

*Stipules.*—Size: 14 mm–16 mm. Color: Yellow-Green Group 146C. Stipitate glands: Located along margins.

*Petiole.*—Length: 20 mm–25 mm. Color: Green Group 137B. Underneath: Generally smooth, with 1–2 small prickles. Margins: With limited numbers of stipitate glands.

*Rachis.*—Color: Green Group 137B. Underneath: Generally smooth, with several small prickles. Margins: Small numbers of stipitate glands.

*Leaflet.*—Edge: Serrated. Shape: Ovate. The leaflet's apex is acuminate. The leaflet's base is rounded. Arrangement: The leaflets are arranged in an odd-pinnate formation. Venation: The leaflets are veined in a reticulate pattern. Texture: Upper side of leaflet is moderately glossy. Lower side of leaflet is matte.

Disease resistance: Above average resistance to mildew and black spot, under normal growing conditions in Jackson County, Oreg.

Cold hardiness: 'POULbota' has been found to be resistant to damage from cold in USDA Zone 8 and USDA Zone 7.

We claim:

1. A new and distinct variety of rose plant of the climbing class, substantially as herein illustrated and described as a distinct an novel rose variety due to its abundant, blush flowers with colorful anthers, vigorous growth, and disease resistant foliage.

* * * * *

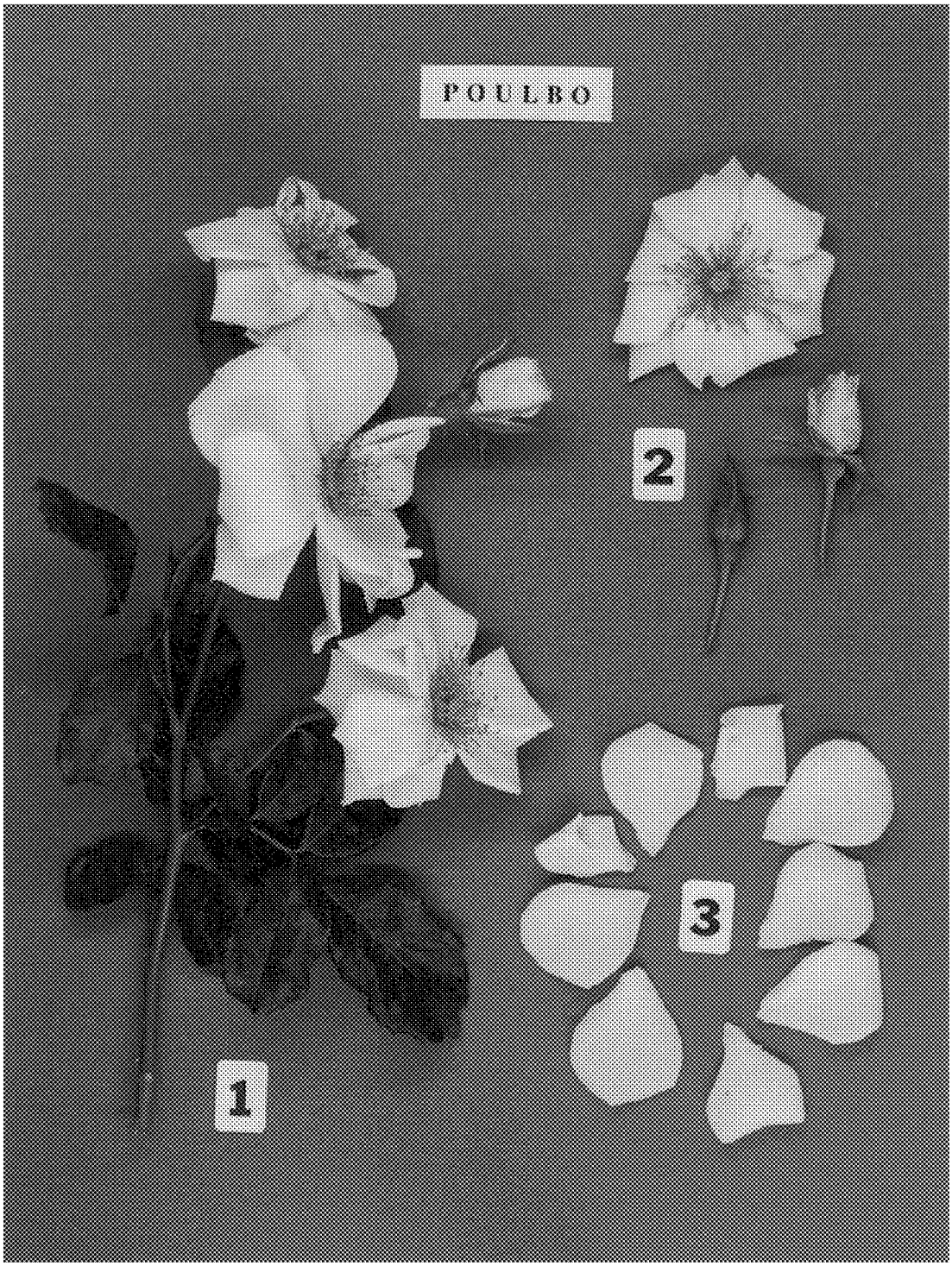
POULBO
2
3
1

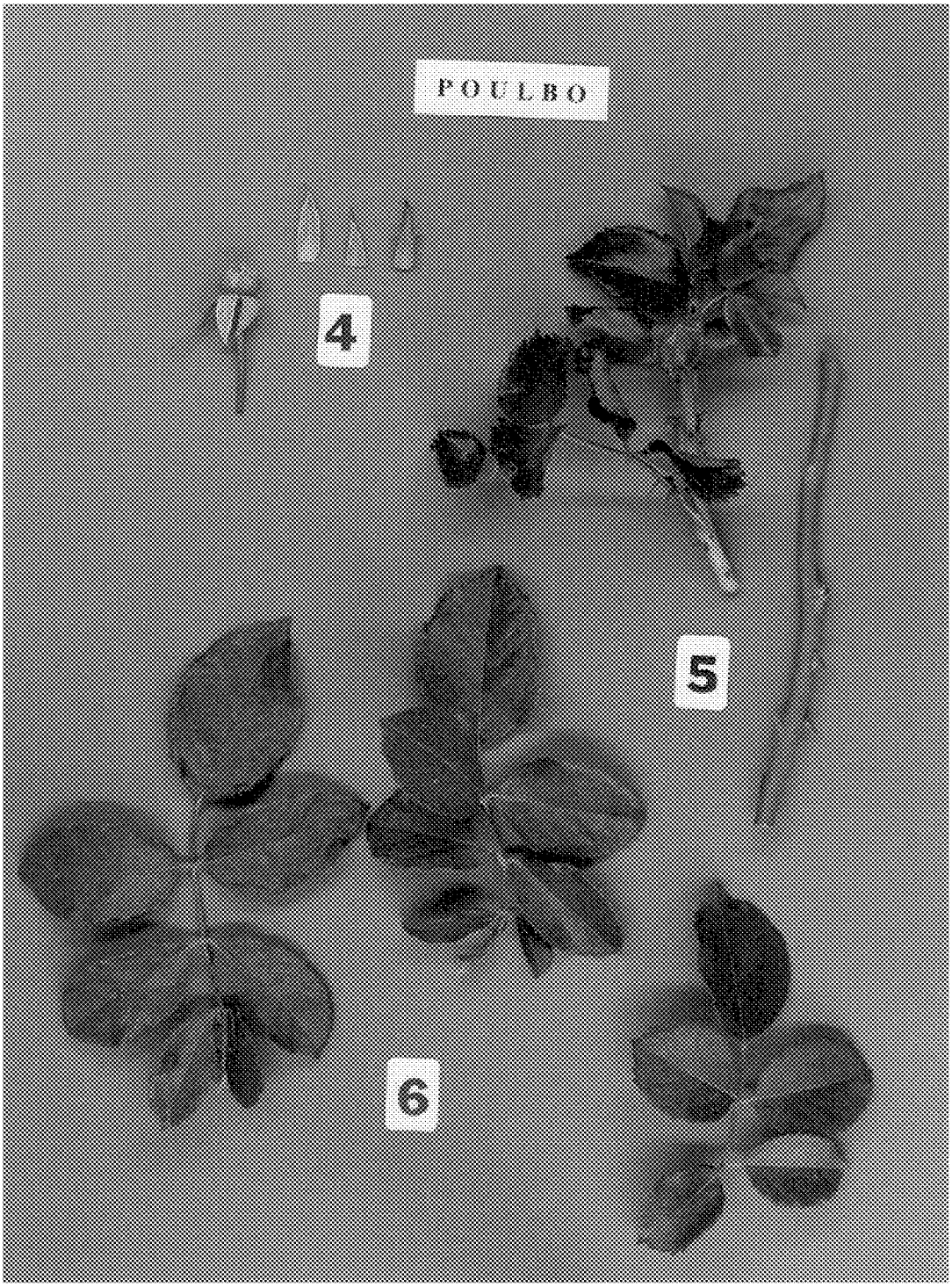
POULBO
4
5
6